United States Patent [19]

Eickmann

[11] Patent Number: 4,889,608

[45] Date of Patent: Dec. 26, 1989

[54] ELECTRODE SYSTEM

[75] Inventor: Guenter Eickmann, Grove City, Pa.

[73] Assignee: Pine Instrument Company, Grove City, Pa.

[21] Appl. No.: 12,885

[22] Filed: Feb. 10, 1987

[51] Int. Cl.[4] .................... C25B 9/02; G01N 27/46
[52] U.S. Cl. ............................ 204/212; 204/400;
 204/435
[58] Field of Search .................. 204/400, 212, 435

[56] References Cited

U.S. PATENT DOCUMENTS

| 2,401,287 | 5/1946 | Yant et al. | 204/212 |
|---|---|---|---|
| 2,486,871 | 11/1949 | Osterheld | 204/197 |
| 2,666,027 | 1/1954 | Vallett | 204/197 |
| 3,492,216 | 1/1970 | Riseman et al. | 204/419 |
| 3,743,590 | 7/1973 | Roll | 204/212 |
| 3,798,056 | 3/1974 | Okinaka et al. | 204/212 |
| 3,882,011 | 6/1975 | Hines et al. | 204/195 R |
| 4,314,896 | 2/1982 | Binder et al. | 204/195 R |
| 4,497,693 | 2/1985 | Ogura et al. | 204/212 |
| 4,545,873 | 10/1985 | Blake et al. | 204/212 |
| 4,605,626 | 8/1986 | Beck | 204/212 |

OTHER PUBLICATIONS

RDE3 Operating Instruction, undated.
ASR2 Rotator Data Sheet, 11/83.
Electrodes Data Sheet, 8/83.
Square-Wave Reprint ©1983.

Primary Examiner—T. Tung
Attorney, Agent, or Firm—Calfee, Halter & Griswold

[57] ABSTRACT

A quick change electrode assembly for immersion in an electrolytic fluid includes an electrode disc frictionally mounted in a TFE fluorocarbon plug disc holder in a sealed interference fit. Part of the disc holder is selectively assembled in and sealed to a PCTFE adaptor. The adaptor is threadedly mounted on the lower end of a spindle. A contact stud is removably secured on the spindle and extends into the plug disc holder. A coil spring is secured at one end to the contact stud and engages the electrode disc at its other end to complete a conductive path therebetween. The electrode disc may selectively be removed by a tool kit from the unassembled disc holder and quickly replaced with a new electrode disc. The disc holder may then be reinstalled on the adaptor, with the coil spring making a reliable electrical connection with the new electrode disc. The spindle is rotatably supported in a housing, and is rotated by a drive motor, with the spindle being electrically isolated from the drive motor and from the housing, to enable the spidle to form part of a conductive circuit for the electrode.

25 Claims, 4 Drawing Sheets

ELECTRODE SYSTEM

FIELD OF THE INVENTION

The present invention generally relates to electrodes for immersion in electrolytic fluids and specifically relates to a rotatable electrode wherein the conductive path is isolated from the motor and the electrode disc may be quickly changed.

BACKGROUND OF THE INVENTION

A standard electrode offered by the assignee of the present invention includes a noble metal electrode disc soldered to a stainless steel substrate. The substrate includes a smaller diameter disc projection and a larger diameter body section. The substrate body section has a threaded blind end bore adapted threadedly to receive part of the electrode arbor or spindle. The substrate and electrode disc are inserted in a TFE fluorocabon sleeve. This sleeve is shrunk fit into an interference fit with the stainless steel substrate to form a seal therebetween. This plastic covered electrode has been successful, but the electrode disc is permanently connected to the stainless steel substrate which in turn is sealed to the TFE fluorocarbon sleeve. Therefore, the entire electrode must be removed and replaced by a different electrode if a different electrode disc is required for comparative testing functions or for different applications.

SUMMARY OF THE INVENTION

A principal object of the present invention is to provide a quick change electrode subassembly wherein different electrode discs may be used with and sealed to the same disc holder or different disc holders may readily be used. For this purpose, a TFE fluorocarbon plug disc holder is provided which may be assembled on and removed from an adaptor body threadedly joined to the spindle. This disc holder has a bore therethrough which receives a contact stud threadedly joined to the bottom of the spindle. The contact stud has a spring mounted on the bottom thereof which reliably contacts the electrode disc received in a counterbore disc pocket on the TFE fluorocarbon disc holder to establish a conductive path between the disc and contact stud. Electrode discs may be inserted in and removed from this counterbore pocket when the disc holder is unassembled, and different disc holders may be installed on and removed from the same adaptor.

Another object of the present invention to provide a new and improved rotator structure for rotating an electrode in an electrolytic fluid. The rotator structure includes a drive motor which is electrically isolated from the electrode spindle. A housing has bearings and thrust washers therein rotatably to receive the upper end of the spindle. This housing includes a special plastic drive coupling providing a relatively rigid connection between the spindle and the motor drive shaft while electrically isolating the motor drive shaft from the spindle. Additionally, the spindle is supported in the housing in a manner which electrically isolates the spindle from the housing. Thus, the spindle can form part of a conductive circuit, while being electrically isolated from both the motor and the housing.

It is yet another object of the present invention to provide a tool kit for installing and removing the electrode disc from the plug disc holder. This tool kit includes a base which can be utilized to insert the disc into the plug disc holder and to remove the disc from the plug disc holder in conjution with an associated tool.

The invention, then, comprises the features hereinafter fully described and particularly pointed out in the claims, the following description and annexed drawings setting forth in detail certain illustrative embodiments of the invention, these being indicative, however, of but a few of the various ways in which the principals of the invention may be embodied.

DETAILED DESCRIPTION OF THE PREFERRED EMBODIMENT

Figure 1:
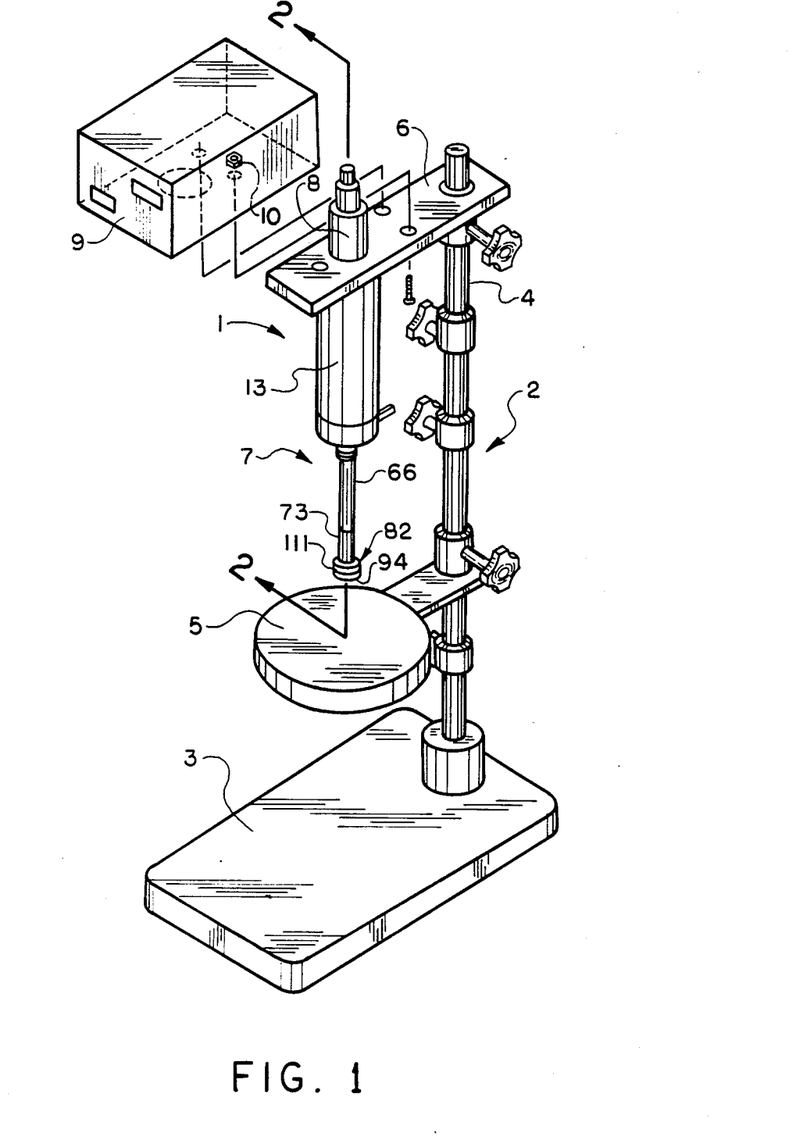
FIG. 1 is a perspective of the quick change electrode assembly mounted on a test stand.

Turning now in more detail to the drawing and initially to FIG. 1, the rotating electrode test assembly, indicated generally at 1, includes a test stand, indicated generally at 2. The stand includes a base 3 supported on a laboratory bench or the like. A vertical column 4 is mounted on and extends upwardly from the base 3. A platform 5 is selectively vertically adjustable on and cantilevered from the column 4. The platform 5 supports a cell or flask (not shown) containing an electrolytic fluid in which the electrode is immersed. A support bracket 6 is also vertically adjustable on and cantilevered from the column 4 of stand 2. The support bracket 6 mounts the rotatable electrode assembly indicated generally at 7.

The rotatable electrode assembly 7 includes an electric motor 8 supported on and extending above the support bracket 6. The electric motor 8 is preferably a small DC motor with tachometer feedback control. The motor is normally enclosed in a control box 9 removable secured to the bracket 6 by fasteners 10. The rotatable drive shaft 11 of motor 8 extends downwardly through a hole 12 in the support bracket into the upper end of spindle housing 13. The spindle housing 13 is secured to support bracket 6 by fasteners 14 and extends downwardly therefrom.

Figure 2:
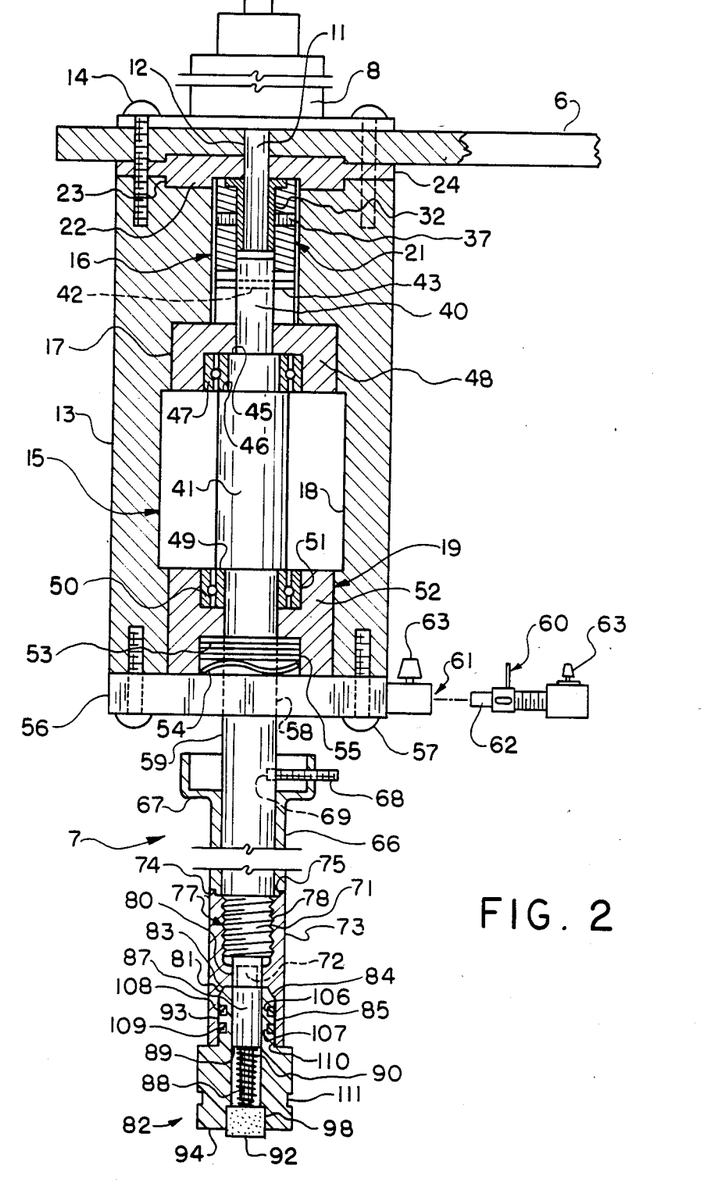
FIG. 2 is a vertical cross section of the electrode assembly and spindle housing taken generally along the plane 2—2 in FIG. 1.

The spindle housing 13, which is preferably made of aluminum, has a stepped bore therethrough, indicated generally at 15. The stepped bore includes, from top to bottom, a coupling section 16, an upper bearing section 17, a central section 18 and a lower bearing and washer section 19. The lower end of motor drive shaft 11 is received in a drive coupling indicated generally at 21.

The drive coupling 21 is contained in the coupling section 16 of stepped housing bore 15. The upper containment of the drive coupling is achieved by backing plate 22 being received in a counter bore 23 in the top of spindle housing 13. The backing plate 22 is mounted on a spacer block 24 fixedly secured to the support bracket 6 by fasteners 14.

Figures 3, 4, 5, 6:
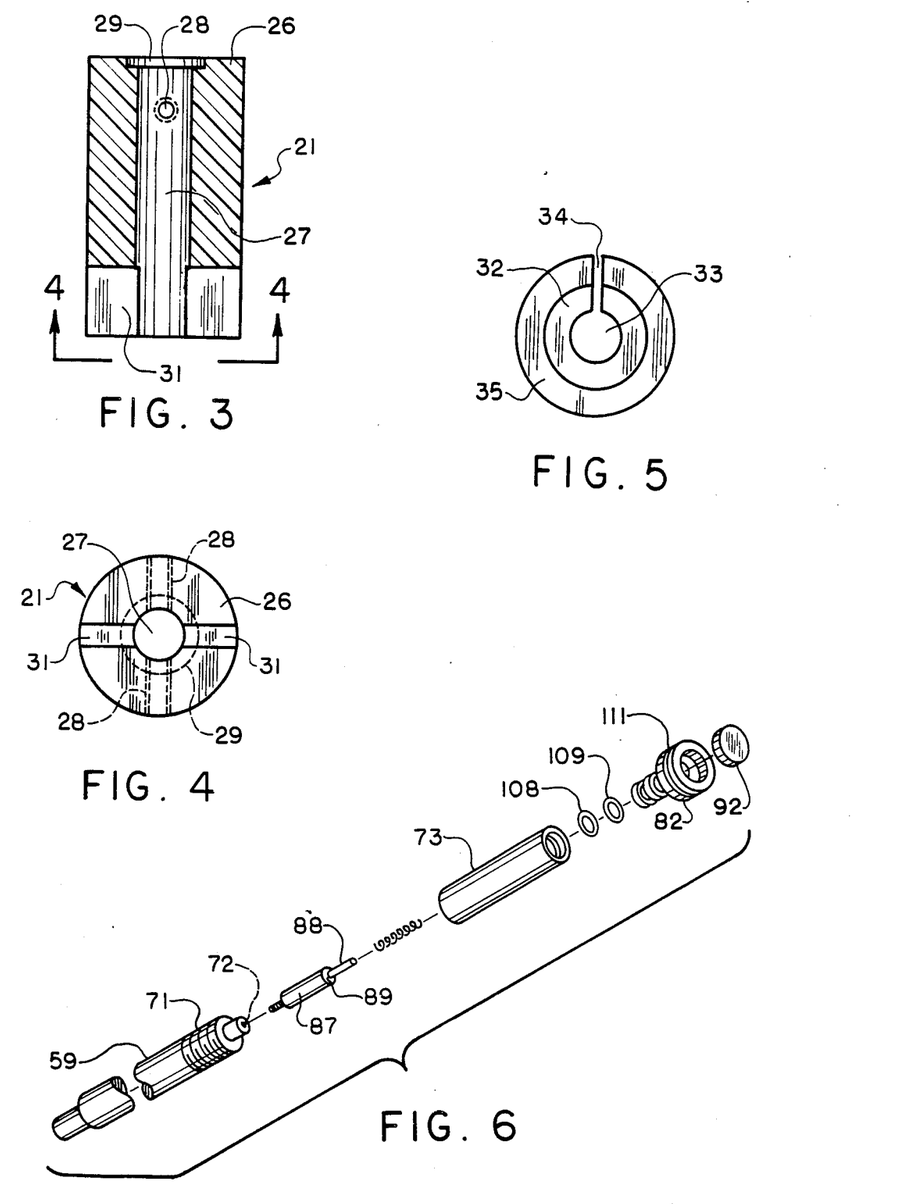
FIG. 3 is a cross section of the drive coupling adapted to be inserted in the main spindle housing bore.
FIG. 4 is a bottom view of the drive coupling taken generally along the plane 4—4 in FIG. 3.
FIG. 5 is a bottom view of the clamp adapted to be inserted into the coupling to connect the motor drive shaft to the coupling.
FIG. 6 is a telescopic perspective of some of the components of the electrode assembly of the present invention in unassembled condition.

Referring to FIGS. 2 through 4, the drive coupling 21 includes a generally tubular body 26 having a bore 27 extending therethrough. The coupling body 26 is preferably made from a acetal homopolymer thermoplastic, which is sold under the trademark DELRIN by DuPont. The acetal homopolymer thermoplastic is light weight and electrically non-conductive The coupling body 26 adjacent its upper end has two diametrically aligned threaded holes 28 therethrough the intersect with bore 27. A counterbore 29 coaxially communicating with bore 27 is provided in the upper end of coupling body 26 adjacent the two opposed threaded holes 28. The lower end of the coupling body 26 has two diametrically opposed, blind end slots 31 extending therethrough as best shown in FIG. 3. The slots 31 are open at the bottom end of the coupling 21 as shown in FIG. 3 for assembly purposes as will be defined in more detail below.

The coupling 21 has tubular clamp 32 received therein as best shown in FIGS. 2 and 5. The clamp is preferably made of brass and is C-shape in plan as shown in FIG. 5. This C-shape is defined by a tubular bore 33 and a radial slot 34 extending outwardly from the bore along the entire length of clamp 32. The upper end of the clamp 32 has a flange 35 extending radially outwardly therefrom.

The clamp 32 is positioned in bore 27 of coupling body 26 with the flange 35 being received in counter bore 29 properly to position the clamp relative to the coupling body 26. The drive shaft 11 is received in the bore 33 of brass clamp 32. Two fasteners 37 are threaded in opposite directions through aligned holes 28 in coupling body 26 to bear against the outer diameter of the clamp 32. The fasteners advancing in opposite directions radially constrict the brass clamp 32 by reducing the gap in slot 34. The radial constriction of the C-shape clamp results in its inner diameter tightly engaging the motor drive shaft 11 to provide a tight clamp therewith. Therefore, rotation of the drive shaft 11 will be imparted to the coupling 21.

The lower end of bore 27 of coupling 21 receives the upper end 40 of spindle 41. The upper spindle end 40 has a hole 42 extending therethrough. A drive pin 43 extends through the aligned slots 31 in the coupling body 26 and the hole 42 in upper spindle end 40. The drive pin 43 is preferably a straight split pin which is radially compressed when inserted through slots 31, to provide a tight fit and a relatively rigid drive connection between the coupling 21 and the spindle 41. The pin 43 thus rotatably secures the spindle 41 to the coupling 21, and rotation of coupling 21 will impart rotation to the spindle. Therefore, coupling 21 provides a drive connection between the drive shaft 11 and spindle 41 to impart the rotation of drive shaft 11 to the spindle. However, the motor drive shaft 11 and the upper spindle end 40 are axially spacially separated in the coupling as illustrated in FIG. 1. Because of this separation and the coupling body material being electrically non-conductive, the drive shaft 11 is electrically insulated form the spindle 41. Further, as will be clear from the foregoing discussion, the coupling between the motor's output shaft and the spindle provides a relatively rigid mechanical coupling between those members. The term "relatively rigid" coupling as used herein, means a coupling which drives the spindle in a 1:1 relationship with the motor's output shaft.

A coupling shoulder 45 on spindle 41 assists in aligning hole 42 with the top of coupling slots 31 and further provides a lower containment for coupling 21 in the coupling section 16 of stepped bore 15. A second shoulder 46 on spindle 41 serves to support the upper bearings 47 mounted in cup shape sleeve 48. The cup shape sleeve 48, which is preferably made from an acetal homopolymer thermoplastic, is received in upper bearing section 17 of the stepped bore 15 through spindle housing 13. The upper bearings 47 cooperate with lower bearings 50 rotatably to mount spindle 41 in the spindle housing 13.

The lower bearings 50 are received in the upper compartment 51 of bearing and washer sleeve 52. This bearing and washer sleeve 52, which is also preferably made from an acetal homopolymer thermoplastic, is received in the lower bearing section 19 of stepped bore 15 in the main housing 13. A third shoulder 49 on spindle 41 rests on the top surface of bearings 50 to assist in locating and supporting the spindle 41. Washers 53 and spring washer 54 are received in the lower compartment 55 of bearing and washer sleeve 52 to take up any axial loads or thrust on spindle 41 in use. The washers 53 and spring washer 54 are retained in place within sleeve 52 by plastic brush plate 56.

Plastic brush plate 56 is secured to the bottom end of spindle housing 13 by fasteners 57. The plastic brush plate 56 has a circular hole 58 therein through which the main spindle shaft 59 of spindle 41 passes. A brush lead assembly, indicated generally at 60, is partially received in brush plate 56 as indicated by the arrow 61. The brush lead assembly has brushes 62 that continuously engage spindle shaft 59 to provide conductive contact with the shaft. The brushes 62 are part of an electrically conductive path leading from the spindle through the brush lead assembly 60 to the exposed terminal 63. A lead in the testing circuit is selectively connected to terminal 63. Thus, the electrical conductivity passes from spindle shaft 59 to the brush lead assembly 60 and then to the testing circuit by suitable electrical connection with terminal 63. This electrical take off from the spindle shaft 59 in conjunction with the insulation provided by drive coupling 21 electrically isolates the motor 8 from the conductivity of the electrode assembly. Further, the bearing and washer sleeve 52, which is electrically non-conducting, electrically isolates the spindle shaft 59 from the aluminum housing 13.

The electrode assembly 7 is removably connected to the bottom end of the spindle shaft 59 as best shown in FIGS. 2 and 6. The spindle shaft 50 is protectively covered by tubular spindle cover 66, preferably made of TFE fluorocarbon plastic. The spindle cover 66 has an annular retaining collar 67 at its upper end. A set screw 68 is threaded through a threaded hole in the retaining collar 67. The leading end of screw 68 is received in a recess 69 in spindle shaft 59 to retain the cover 66 in proper position relative to the spindle shaft 59.

The lower end of the spindle shaft 59 has an externally threaded male section 71 and a reduced diameter internally threaded female section 72. An adaptor body 73 is mounted on the lower end of spindle shaft 59.

The adaptor body 73 is preferably made from polychlorotrifluoroethylene (PCTFE) fluroplastic material, which is sold under the trademark Kel-F by The Minnesota Mining and Manufacturing Company. Adaptor body 73 has upper annular skirt 74 received in annular recess 75 at the bottom of tubular spindle cover 66 to provide a tight connection therebetween. The adaptor body 73 has a specially configured bore, indicated generally at 77, passing therethrough. The adaptor body bore 77 has an upper female threaded section 78 threadedly mating with the male section 71 on spindle shaft 59 to hold the adaptor body in place. The adaptor body bore 77 further includes a central section 80 receiving the female threaded section 72 of spindle shaft 59 and a lower section 81 selectively receiving part of a plug disc holder, indicated generally at 82. The lower section 81 of bore 77 in adaptor body 73 includes a frusto-conical upper end 83 and a cylindrical lower end 84 having annular recess 85 therein.

The female threaded section 72 of spindle shaft 59 receives the upper male threads on contact stud 87. The contact stud 87, which is preferably made of 303 stainless steel, is thus in physical and conductive contact with spindle shaft 59. The lower end of contact stud 87 has a guide projection 88 and a spring shoulder 89. A spring 90, preferably made of stainless steel, has two flat coil ends to enhance surface contact. The upper flat end of spring 90 is secured to shoulder 89 by conductive, silver contact epoxy cement or the like. The spring 90 encircles the guide projection 88 and extends downwardly therefrom as shown in FIG. 2. The lower end of spring 90 makes physical and conductive contact with an electrode disc 92 when the plug disc holder 82 is selectively mounted on and sealed to adaptor body 73.

The plug disc holder 82 is preferably made from virgin TFE fluorocarbon material, which is sold under the trademark TEFLON by DuPont. Plug disc holder 82 has a bore 93 extending therethrough to receive the contact stud 87 and spring 90 when the disc holder is assembled. The disc holder 82 includes a lower, generally cylindrical, exposed section 94, upwardly extending body portion 95 and a frusto-conical tip 96 (See FIG. 7). The lower exposed section 94 has a counterbore coaxial to bore 93 to form a pocket 98 therein selectively to receive the electrode disc 92. The disc pocket 98 is designed to have an internal configuration complementing the external configuration of the electrode disc 92. The internal dimensions of the disc holder counterbore pocket 98 are preferably slightly smaller than the external dimensions of the electrode disc resulting in a tight frictional interference fit therebetween to form a fluid tight seal. A typical dimensional interference fit would include a dimensional overlap prior to insertion of approximately 0.010 to 0.012 inches, with the overlap increasing for larger electrodes.

The disc is installed in the disc holder by manually press fitting the electrode disc 92 into the counter core pocket 98. Alternatively, the base 100 of an installation and removal tool, indicated generally at 101, can be used. The base 100 on its bottom surface 102 may have a recessed holder 103 formed therein. The recessed holder 103 has an inner diameter or configuration dimensioned approximately to equal the outer diameter or configuration of the electrode disc 92. The recessed holder 103 thus can loosely retain the electrode disc 92 placed therein as illustrated in phantom in FIG. 8.

Figure 8:
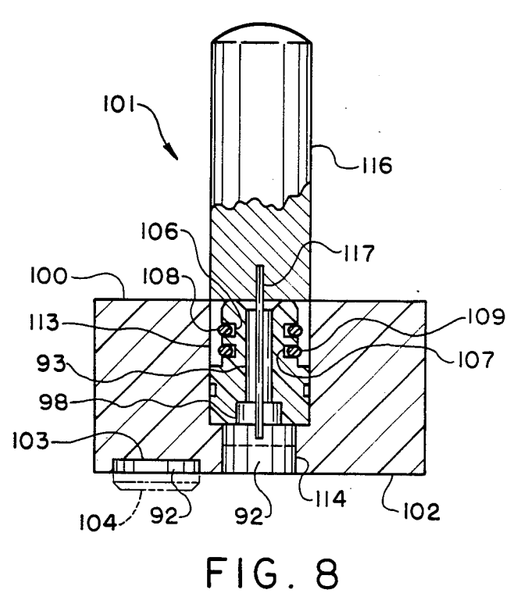
FIG. 8 is an elevation partially in section of the tool kit schematically showing both the electrode disc installation and removal functions.

Preferably, the electrode disc 92 has a chamfered edge 104 designed to facilitate mounting the disc 92 in counterbore pocket 98 in the plug disc holder 82. The tool base 100 with the electrode disc 92 loosely held therein is inverted and pressed against the lower surface of plug disc holder 82. This results in the chamfered edge 104 entering the counterbore pocket 98 until it bottoms out therein. The base 105 is then withdrawn leaving the electrode disc 92 mounted within the counterbore pocket 98 in a fluid tight frictional interference fit.

Figure 9:
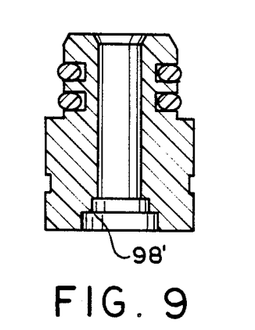
FIG. 9 is a schematic illustration of an alternative form of disc holder.

The disc 92 after insertion into counterbore pocket 98 may either be flush with the bottom surface of disc holder 82 or may extend below the bottom surface, as illustrated in FIG. 2. In either event, during testing, the disc 92 is submerged in the electrolytic fluid to set up an electrolytic current path through the fluid to a reference electrode also submerged in the fluid. The frictional interference seal between the disc and counterbore pocket precludes the corrosive fluid from leaking or seeping into the bore 93 of the disc holder. The disc 92 and counterbore pocket 98 may be machined for a high degree of concentricity to provide the interference seal through a 360° circumferential extend and through the depth of the counterbore pocket in an axial extend. Further, the counterbore pocket may have a double step configuration, as shown schematically at 98' in FIG. 9, to allow relatively shallow disc insertion and/or to provide additional sponginess to the counterbore pocket during insertion of the electrode disc.

The physical properties of the TFE fluorocarbon disc holder relative to the physical properties of the disc are interrelated with the relative dimensions selected to assure sealed retention therebetween throughout the normal temperature operating range for electrolytic fluid testing. For example, the coefficient of thermal expansion for TFE fluorocarbon is greater than that for the electrode disc which is normally made of metal (e.g. stainless steel) or glassy carbon. Thus, the disc holder will radially expand slightly faster than the disc as the temperature increases. However, the relative dimensions are selected to provide sufficient interference at ambient to retain the fluid tight interference seal as the fluid temperature increases to even 60° or 70° C. Similarly, the physical properties of the TFE fluorocarbon disc holder and PCTFE adaptor body are interrelated with the relative dimensions during design selection to maintain the seal therebetween throughout the normal fluid temperature operating ranges.

Figure 7:
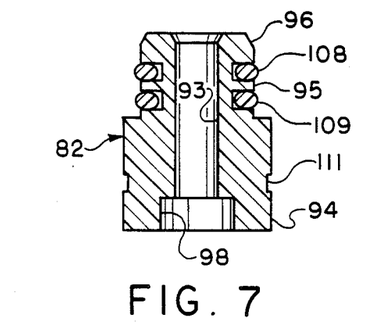
FIG. 7 is sectional illustration, on an enlarged scale, of the disc holder.

To this end, the central body portion 95 of disc holder 82 has two axially spaced annular recesses 106 and 107 in its outer diameter. Recess 106 receives silicon 0-ring seal 108, and recess 107 receives silicon 0-ring seal 109. These 0-ring seals align, position and seal the disc holder 82 to the adaptor 73 when the disc holder is assembled on the adaptor.

During assembly, the frusto-conical tip 96 and main body part 94 are inserted into the lower bore section 81 of the adaptor body 73. Proper alignment and positioning between the plug disc holder 82 and adaptor body 73 are obtained by 0-ring seal 108 and the complimentary geometry of the respective parts. The frusto-conical inserted tip 96 of disc holder 82 abuts the frusto-conical surface 83 of lower bore section 81 in the adaptor body. The upper 0-ring seal 108 carried by the inserted cylindrical body section 95 of disc holder 82 is received in the annular recess 85 of adaptor body 73 to align and position the disc holder relative to the adaptor body. The flange 110 formed by the radially enlarged exposed section 94 of the disc holder 82 also engages the lower end of adaptor body 73 to provide proper relative positioning between the parts. The plug disc holder is sealed to the adaptor body 73 principally by compression of O-ring seal 109 between groove 107 and bore wall 84 in adaptor 73 and secondarily by some compression of O-ring seal 108 between groove 106 and bore wall 84. The outer diameter of the body portion 95 of holder 82 is in close proximity to the inner diameter of the adaptor body throughout the normal fluid temperature operating range to result in the seal 109 always being tightly compressed therebetween to maintain the fluid tight seal.

In assembling the disc holder 82, the contact stud 87 and spring 90 are received in the bore 93. The coil spring 90 has an axial length that would normally be longer than the length of bore 93. Accordingly, when the disc holder is assembled, the electrode disc will engage the spring 90 during insertion and will compress the spring until the disc holder is fully inserted and sealed. This spring compression results in a reliable conductive contact being made between spring 90 and disc 92.

When the plug disc holder 82 is mounted in and sealed to adaptor body 73, the electrode assembly 7 is ready for use. The test is set up by immersing the electrode disc 92 in the electrolytic fluid. The test circuit can be set up to test characteristics of the electrode, the electrolytic fluid, or both, or will be readily apparent to those of ordinary skill in the art. The plug disc holder 82 has a depth penetration notch 111 in its exposed cylindrical section 94. This depth penetration notch 111 serves as a visual indicator to the lab technician as to how far the electrode should be lowered into the electrolytic test fluid by vertically adjusting either support bracket 6 and/or cantilever platform 5. When the electrode disc 92 is properly submerged in the fluid being tested, the path of electrical conductivity in the electrode is through disc 92, spring 90, contact stud 87, spindle shaft 59, brush lead assembly 60 and terminal 63.

When the test is completed and the fluid removed, the plug disc holder 82 may be withdrawn from the adaptor body by manually pulling the plug disc holder to cause the separation. The electrode disc 92 may then be removed and another readily installed. For removal, the electrode disc holder 82 is inserted into bore 113 of bore 114 in tool base 100, as best shown in FIG. 8. To remove the electrode disc from the disc holder so received, a tool is used consisting of handle 116 and an ejector pin 117 mounted on and extending outwardly from the handle. The ejector pin 117 is advanced into the bore 93 of disc holder 82 and the handle is slowly moved downwardly so that the leading end of the ejector pin 117 engages the electrode disc. Continued downward movement of the tool results in the ejector pin forcibly removing the electrode disc 92 from counterbore pocket 98. The electrode disc 92 is free to fall out of the tool kit base 105 through bore 114 as shown in phantom in FIG. 6. A different electrode disc may then be mounted in plug disc holder in the manner described above and the disc holder reassembled on the electrode.

Alternatively, a different plug holder 82 can be assembled on the adaptor 73. The different plug holder can have a counterbore pocket larger, smaller, deeper, shallower or equal to the size of pocket 98 and/or can have pocket geometry the same as or different than the geometry of pocket 98 (Compare e.g. the plug disc holders of FIGS. 7 and 9). Accordingly, these different plug holders can receive electrode discs or electrode cylinders of different sizes, shapes and materials to enhance the flexibility of the electrode assembly to many different applications and tests. The term electrode disc as used herein is meant generically to include these various sizes and shapes of electrode bodies. The different plug holder has the same diameter and sealing structure for its inserted body portion 95 and tip 96 to allow it to be pushed into and sealed to adaptor 73. The spring 90 is compressed slightly in this insertion to provide a reliable conductive contact with electrode discs of all sizes and shapes.

Although the assembly steps for the electrode assembly are believed clear from the above, the following brief description of the assembly sequence is added for completeness. The motor 8 is lowered onto bracket 6 with drive shaft 11 extending through hole 12. The coupling 21 with clamp 32 inserted therein is then positioned around drive shaft 11. The upper end of coupling 21 engages the backing plate 22 for proper positioning, with the backing plate 22 and spacer 24 being sandwiched between the coupling and bracket. Screws 37 are then run into coupling 21 in opposite directions to engage and radially constrict the clamp about drive shaft 11 to connect the spacer to the drive shaft 11.

As a subassembly, the spindle 41, upper bearing sleeve 48, lower bearing and washer sleeve 52, housing 13, plastic brush plate 56 and brush lead 60 have been preassembled with the bearings and washers shown. The pin 43 is installed in hole 42 in the upper spindle end 40 in this subassembly. The subassembly is then raised with the exposed ends of pin 43 being received in the blind end slots 31 in coupling 21 to allow the subassembly to be elevated until the top of the housing 13 engages spacer plate 24. Fasteners 14 are then run through the bracket 6 and spacer 24 into tapped holes in the housing 13 to connect the subassembly to the bracket 6 in properly assembled relationship.

The spindle cover 66 is secured to the spindle shaft 59 by set screw 68. The contact stud 87 is threaded onto the female threaded portion of spindle shaft 59, with the spring 90 secured thereto. The adaptor 73 is then progressively elevated past the surrounded spring 90, contact stud 87 and female threaded section 72 for threaded connection to externally threaded male section 71. The disc holder 82 is finally inserted into the assembled adaptor to complete the electrode assembly. The components assembled on the spindle shaft 59 below brush plate 56 can either be preinstalled as part of the subassembly or can be installed after the subassembly is mounted on bracket 6.

It will be apparent from the foregoing that changes may be made in the details of construction and configuration without departing from the spirit of the invention as defined in the following claims. For example, the quick change electrode disc assembly can be used on a stationary electrode arbor as well as on the rotatable spindle. A stationary arbor provided with a male threaded section and female threaded section at its lower end would be readily adaptable to the contact stud, spring, adaptor and disc holder of this invention.

I claim:

1. A quick change electrode assembly for immersion in an electrolytic fluid comprising an arbor, an adaptor mounted on the arbor and having a first bore extending therethrough, a contact stud mounted on and in electrical contact with the arbor, a disc holder partially inserted in and sealed to the first bore of the adaptor, said disc holder having a bore receiving the contact stud at one end and frictionally receiving an electrode disc in a fluid tight interference seal at the other end and a spring secured to the contact stud and extending through the disc holder bore into engagement with the electrode disc to complete a conductive path therebetween.

2. The quick change electrode assembly a set forth in claim 1 wherein the disc holder is a TFE fluorocarbon plastic and the adaptor is made of a PCTFE plastic.

3. The quick change electrode assembly of claim 2 wherein the spring is coiled stainless steel, has two flat coil ends respectively to enhance surface engagement with the contact stud and electrode disc and is secured to the contact stud with conductive silver epoxy cement.

4. The quick change electrode assembly of claim 1 wherein the disc holder has an exposed cylindrical portion and a reduced diameter body portion inserted into the first in the adaptor.

5. The quick change electrode assembly of claim 4 wherein the body portion of the disc holder has two axially spaced 0-ring seals thereon, the first 0-ring seal being received in an annular groove in the first bore principally for aligning and positioning the disc holder relative to the adaptor and the second 0-ring seal being compressed against the first bore wall to seal the disc holder to the adaptor.

6. The quick change electrode assembly of claim 5 wherein the body portion of the disc holder has a frustoconical tip cooperating on insertion with a frusto-conical surface in the first bore.

7. The quick change electrode assembly of claim 1 wherein the arbor has a male threaded section selectively threaded for engagement with female threads on the adaptor and has a female threaded section selectively threaded for engagement with male threads on the contact stud.

8. The quick change electrode assembly of claim 7 wherein the disc holder has a counterbore coaxial with the disc holder bore to form a pocket removably receiving the electrode disc in an interference sealed fit.

9. The quick change electrode assembly of claim 8 wherein the arbor is a spindle and a brush lead assembly cooperaties with the spindle to form part of the conductive path for the electrode assembly.

10. The quick change electrode assembly of claim 9 wherein the spindle is rotated by a drive motor electrically insulated from the spindle.

11. The quick change electrode assembly of claim 10 wherein the drive motor has a drive shaft and a plastic insulative coupling connects the drive shaft to the spindle with an axial space therebetween to form an insulated mechanical connection imparting the rotation of the drive shaft to the spindle.

12. The quick change electrode assembly of claim 11 wherein a clamp is inserted in a first end of the coupling and opposed fasteners pass through the coupling adjacent that first end of the coupling to engage and close the clamp tightly around the drive shaft.

13. The quick change electrode assembly of claim 12 wherein the coupling has two diametrically aligned slots in its second end and a drive pin passes through the two slots and a hole in the spindle end received in the second end of the coupling to provide a drive connection therebetween.

14. A quick change electrode assembly of claim 13 wherein the coupling is acetal homopolymer thermoplastic and the clamp is brass.

15. The quick change electrode assembly of claim 9 further comprising a sleeve cover connected to and surrounding the spindle, the sleeve cover having an annular recess on its lower end receiving an annular skirt on the upper end of the adaptor fully to enclose the spindle and contact stud.

16. The quick change electrode assembly of claim 1 wherein the disc holder may be manually separated from and replaced in the adaptor.

17. The quick change electrode assembly of claim 16 wherein the disc holder has a counterbore coaxial with the disc holder bore to form a pocket removably receiving the electrode disc in an interference sealed fit.

18. The quick change electrode assembly of claim 17 wherein the electrode disc may be removed from the disc holder when the disc holder is separated from the adaptor and a new electrode disc may be push fit into an interference seal with the counterbore in the disc holder.

19. The quick change electrode assembly of claim 18 wherein the separated disc holder is placed in a second counterbore in a base and a tool with an ejector pin is inserted into the disc holder bore of the disc holder to push the electrode disc out of the counterbore in the disc holder and through a bore in the base.

20. The quick change electrode assembly of claim 19 wherein the base has means in one surface loosely to hold an electrode disc to allow the one surface of the base to be pressed against the disc holder to install the electrode disc in the counterbore.

21. A quick change electrode assembly for electrolytic fluid testing comprising a rotatable spindle, a contact stud secured to the spindle and a spring mounted on the contact stud and extending into engagement with an electrode disc removably push fit in holder means removably push fit into secured engagement with the rotating spindle.

22. The quick change electrode assembly of claim 21 further comprising a drive motor having a drive shaft and an insulative coupling connecting the drive shaft to the spindle in axially spaced relationship relative to one another.

23. The quick change electrode assembly of claim 22 wherein the holder means include a TFE flurocarbon disc holder receiving the electrode disc and a PCTFE adaptor removably secured to the spindle, the disc holder being removably push fit into sealed engagement with a bore through the adaptor.

24. The quick change electrode assembly of claim 23 wherein the disc holder has a bore receiving the contact stud and spring and has a coaxial counterbore forming a pocket removably receiving the electrode disc.

25. Apparatus comprising an electrode and a rotator structure for rotating the electrode in an electrolyte fluid, said rotator structure comprising a housing, a longitudinally extending spindle of conductive material, means rotatably supporting said spindle in said housing, said spindle having a portion in electrical contact with said electrode and another portion connected with a circuit contact to establish a conductive path in said spindle, a motor having a rotatable output shaft disposed at least partially in said housing, and means disposed in said housing for coupling said output shaft with said spindle, said coupling means providing a relatively rigid mechanical drive between said output shaft and said spindle, said coupling means being at least partially formed of electrically nonconductive material and being adapted to electrically isolate said output shaft from said spindle, and said means rotatably supporting said spindle in said housing also being adapted to electrically isolate said spindle from said housing.

* * * * *

UNITED STATES PATENT AND TRADEMARK OFFICE
CERTIFICATE OF CORRECTION

PATENT NO. : 4,889,608

DATED : December 26, 1989

INVENTOR(S) : Eickmann, Guenter

It is certified that error appears in the above-identified patent and that said Letters Patent is hereby corrected as shown below:

Column 9, line 5, delete "a" and insert "as".

Column 9, line 17, after "first" insert "bore".

Column 9, line 41, delete "cooperaties" and insert "cooperates".

Signed and Sealed this

Tenth Day of September, 1991

Attest:

HARRY F. MANBECK, JR.

Attesting Officer

Commissioner of Patents and Trademarks